United States Patent [19]

Fuess

[11] Patent Number: Plant 6,987

[45] Date of Patent: Aug. 15, 1989

[54] CHRYSANTHEMUM PLANT NAMED BORDEAUX

[76] Inventor: Janet S. Fuess, 9011 Red Hill Rd., New Hartford, N.Y. 13413

[21] Appl. No.: 141,252

[22] Filed: Jan. 6, 1988

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A chrysanthemum plant named Bordeaux, characterized by its purple ray floret color, almost fully double flowers with few disc florets, very dark green glossy foliage, compact cushion habit, seven week flower response, freely branching and floriferous flowering, and its early flowering outdoors in natural season.

1 Drawing Sheet

1

The present invention comprises a new and distinct cultivar of *Chrysanthemum morifolium,* Ramat., hereinafter referred to by the cultivar name Bordeaux.

Bordeaux is a product of a planned breeding program which had the objective of creating a new chrysanthemum cultivars with freely branching compact cushion habit, early flower response and purple decorative flowers, making it suitable for production as a garden variety. Such traits in combination were not present or needed improvement in previously available commercial cultivars.

Bordeaux was originated from a hybridization made by applicant in a controlled breeding program in New Hartford, N.Y. in September 1985. The female parent was Debonaire, disclosed in U.S. Plant Pat. No. 5,324. The male parent of Bordeaux was an unnamed seedling. Bordeaux was discovered and selected as one flowering plant within the progeny of the stated parentage by applicant in August 1986 in a controlled environment in New Hartford, N.Y.

The first act of asexual reproduction of Bordeaux was accomplished when vegetative cuttings were taken from the initial selection in March 1987 in a controlled environment in New Hartford, N.Y. by a technician working under formulations established and supervised by applicant. Horticultural examination of selected units initiated in August 1987 has demonstrated that the combination of characteristics as herein disclosed for Bordeaux are firmly fixed and are retained through successive generations of asexual reproduction.

The following traits have been repeatedly observed and are determined to be basic characteristics of Bordeaux, which in combination distinguish this chrysanthemum as a new and distinct cultivar:

1. Purple ray floret color.
2. Almost fully double flower with only a few disc florets present.
3. Very dark green glossy foliage.
4. Fully expanded ray florets approximately 20–26 mm long and 6–7 mm wide.
5. Average of 370 ray florets per capitulum.
6. Capitulum 4–6 cm in diameter.
7. Seven week flower response.
8. Performs well in the outdoor garden, flowering early in natural season.
9. Compact cushion habit, making it suitable for production in 4″ to one gallon containers.
10. Freely branching and flowering.

2

Bordeaux has not been observed under all possible environmental conditions. The phenotype may vary significantly with variations in environment such as temperature, light intensity, and day length. The following observations, measurements and comparisons describe plants grown in New Hartford, N.Y. under greenhouse conditions which approximate those generally used in commercial practice.

Of the many commercial cultivars known to the present inventor, the most similar in comparison to Bordeaux is its maternal parent Debonaire. In comparison to Debonaire, Bordeaux has darker, glossy foliage; the ray florets are more quilled; and the flower color is a darker purple. The compact growth habit is similar to the same characteristic of Debonaire.

The accompanying photographic drawing shows typical inflorescence and foliage characteristics of Bordeaux. The drawing is a black and white photograph with one flower showing the true color of Bordeaux.

In the following description, color references are made to The Royal Horticultural Society Colour Chart. The color values were determined at approximately 4:30–5:00 p.m. on Sept. 28, 1987 under fluorescent light at Parrish, Fla.

Classification:

*Botanical.*—*Chrysanthemum morifolium,* Ramat., cv. Bordeaux.

*Commercial.*—Decorative garden mum.

INFLORESCENCE

A. Capitulum:

*Form.*—Flat.

*Type.*—Double.

*Diameter across face.*—4–6 cm.

B. Corolla of ray florets:

*Color (general tonality from a distance of three meters).*—Purple.

*Color (upper surface).*—61A-B.

*Color (under surface).*—63D.

C. Corolla of disc florets:

*Color (mature).*—Yellow.

*Color (immature).*—Yellow-green.

D. Reproductive organs:

*Androecium.*—Very few; present in disc florets only.

*Gynoecium.*—Present in both disc and ray florets.

PLANT

A. General appearance:

*Height.*—25–35 cm when grown in a 7½" pot. Height can vary depending upon growing conditions, growth regulator applications, and other cultural practices.

B. Foliage:

*Color* (*upper surface*).—147A.

*Color* (*under surface*).—147B.

Shape.—Ovate with cleft margins.

I claim:

1. A new and distinct cultivar of chrysanthemum plant named Bordeaux, as illustrated and described, and parts thereof.

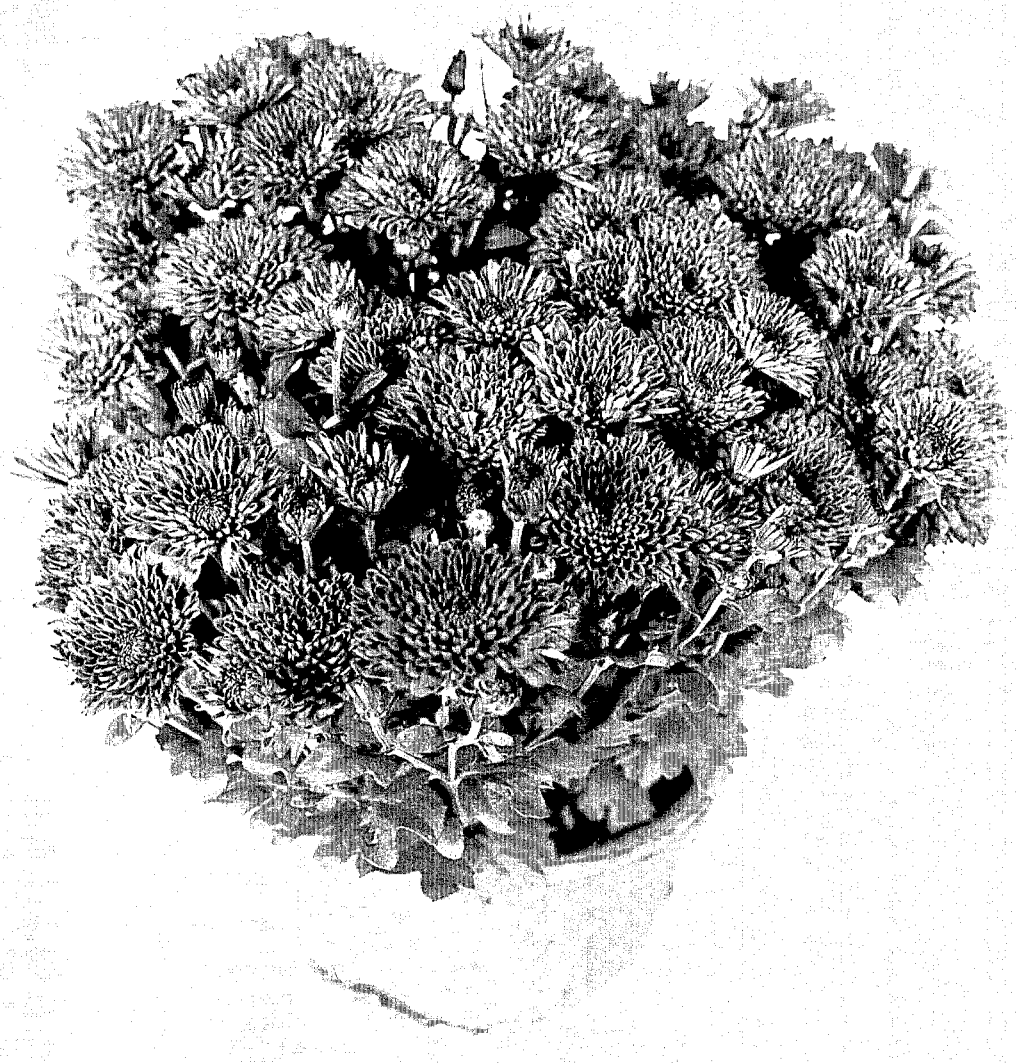

* * * * *